US008157805B2

(12) United States Patent
Re et al.

(10) Patent No.: US 8,157,805 B2
(45) Date of Patent: Apr. 17, 2012

(54) APPARATUS AND METHOD FOR THE REPAIR OF ARTICULAR CARTILAGE DEFECTS

(75) Inventors: Paul Re, Boston, MA (US); Mark A. Johanson, Littleton, MA (US); Peter F. Marshall, Bolton, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 658 days.

(21) Appl. No.: 10/812,609

(22) Filed: Mar. 30, 2004

(65) Prior Publication Data

US 2004/0181232 A1    Sep. 16, 2004

Related U.S. Application Data

(63) Continuation of application No. 10/261,899, filed on Oct. 1, 2002, now Pat. No. 6,712,822.

(60) Provisional application No. 60/326,293, filed on Oct. 1, 2001.

(51) Int. Cl.
*A61F 2/46* (2006.01)

(52) U.S. Cl. .................................. 606/86 R

(58) Field of Classification Search ............ 606/86, 606/72, 75, 219, 70, 71, 280–289, 213, 215, 606/220, 86 A, 86 B, 86 R, 87–105.5, 108
See application file for complete search history.

(56) References Cited

U.S. PATENT DOCUMENTS

| 4,060,089 | A | * | 11/1977 | Noiles | 606/220 |
|---|---|---|---|---|---|
| 4,512,038 | A | | 4/1985 | Alexander et al. | |
| 4,548,202 | A | | 10/1985 | Duncan | |
| 4,776,328 | A | * | 10/1988 | Frey et al. | 606/326 |
| 4,932,973 | A | | 6/1990 | Gendler | |
| 4,976,715 | A | | 12/1990 | Bays et al. | |
| 5,139,499 | A | * | 8/1992 | Small et al. | 606/301 |
| 5,370,650 | A | * | 12/1994 | Tovey et al. | 606/151 |
| 5,634,926 | A | * | 6/1997 | Jobe | 606/281 |
| 5,690,676 | A | * | 11/1997 | DiPoto et al. | 606/232 |
| 5,769,899 | A | | 6/1998 | Schwartz et al. | |
| 6,179,840 | B1 | | 1/2001 | Bowman | |
| 6,187,009 | B1 | * | 2/2001 | Herzog et al. | 606/75 |
| 6,235,034 | B1 | * | 5/2001 | Bray | 606/71 |
| 6,251,143 | B1 | | 6/2001 | Schwartz et al. | |
| 6,267,772 | B1 | * | 7/2001 | Mulhauser et al. | 606/151 |
| 6,283,980 | B1 | | 9/2001 | Vibe-Hansen et al. | |
| 6,533,454 | B1 | * | 3/2003 | Kaikkonen et al. | 378/205 |
| 6,620,163 | B1 | * | 9/2003 | Michelson | 606/286 |

FOREIGN PATENT DOCUMENTS

| EP | 1 129 675 A | 9/2001 |
|---|---|---|
| WO | WO 96/24302 A | 8/1996 |

* cited by examiner

*Primary Examiner* — Gary Jackson
*Assistant Examiner* — Lindsey Bachman

(57) ABSTRACT

An encapsulation device for repair of articular cartilage defects includes a body for disposition adjacent a bone in an area of the cartilage defect, and elongated leg structure extending from the body and for disposition in the bone in the area of the cartilage defect. The leg structure is provided with a length which is a plurality of magnitudes greater than a thickness of the body, and is of a generally conical configuration.

10 Claims, 19 Drawing Sheets

APPARATUS AND METHOD FOR THE REPAIR OF ARTICULAR CARTILAGE DEFECTS

REFERENCE TO PENDING PRIOR PATENT APPLICATIONS

This is a continuation of prior U.S. patent application Ser. No. 10/261,899, filed Oct. 1, 2002 now U.S. Pat. No. 6,712, 822 by Paul Re et al. for APPARATUS AND METHOD FOR THE REPAIR OF ARTICULAR CARTILAGE DEFECTS, which in turn claims the benefit of U.S. Provisional Patent Application Ser. No. 60/326,293, filed Oct. 1, 2001 by Paul Re and Mark A. Johanson for APPARATUS AND METHOD FOR THE REPAIR OF ARTICULAR CARTILAGE DEFECTS.

FIELD OF THE INVENTION

This invention relates to surgical apparatus and methods in general, and more particularly to surgical apparatus and methods for the repair of articular cartilage defects.

BACKGROUND OF THE INVENTION

Articular cartilage defects have long been a serious problem for patients and orthopedic surgeons. No matter how small the initial defect, it carries with it a high potential for progressing into larger, more symptomatic defects, with the accompanying early arthritis and disabling pain and dysfunction.

Over the years, a number of different procedures have been devised for treating articular cartilage defects.

Articular cartilage defects have traditionally been treated with chondroplasty, shaving, microfracture, abrasion arthroplasty and, most recently, autologous transplantation. Early on, the treatment of articular cartilage defects was principally concerned with preventing a progression of the defect. More recently, attention has been focused on developing ways to actually repair the defect and effect articular cartilage healing.

More particularly, chondroplasty and shaving are principally concerned with removing offending portions of the articular cartilage (e.g., loose flaps, rough edges, etc.) so as to prevent the enlargement of an existing articular cartilage defect. While chondroplasty and shaving have proven helpful in preventing the spread of an existing articular cartilage defect, they do not actually repair the defect or effect articular cartilage healing.

The basic idea behind microfracture and abrasion arthroplasty is to violate the subchondral plate, thereby allowing blood (preferably including marrow cells) to fill the defect and initiate an injury repair. This may be done in a variety of ways well known in the art, e.g., with a rasp to abrade the defect, a pick to pick away the area of the defect, a drill to microdrill the area of the defect, an RF probe (or otherwise) to heat and thereby disrupt the region of the defect, etc. It is known that such a procedure does not actually cause articular cartilage to grow in the defect. Rather, a fibrocartilage/Hyaline cartilage regenerates which, while generally not as good as articular cartilage since it lacks the mechanical properties of the articular cartilage, is certainly better than bare bone. However, a common problem with this technique is that the blood (and marrow) cells do not tend to stay seeded in the defect, since they are commonly wiped away by joint motion and/or other factors.

Autologous cartilage transplant is a potentially attractive alternative for healing articular cartilage defects. This has principally been addressed in two different procedures.

In one procedure, generally referred to as osteochondral grafting, a plug of healthy articular cartilage and underlying bone is harvested from a donor site and transplanted to the defect site. While this technique has proven effective, it typically causes serious damage to the donor site. In addition, it can be difficult to find donor sites with the proper surface profiles, and it can be difficult to properly align the layers (i.e., cartilage and underlying bone) of the graft plug with the layers of the defect site.

In the second procedure, sometimes referred to as autologous cell transplantation, cells from healthy articular cartilage are harvested, multiplied outside the body and then reimplanted at the defect site. This has been accomplished most recently by a system available from Genzyme of Boston, Mass. under the trade name Carticell. However, this system does have its drawbacks: it requires at least two surgical procedures (i.e., one to harvest the cells and one to reimplant them); it is relatively expensive; and there are limits in the size of lesion, and the number of lesions, that can be treated. Also, with this system, the defect generally has to be "contained" in order for the system to be successful.

SUMMARY OF THE INVENTION

Accordingly, one object of the present invention is to provide improved apparatus for the repair of articular cartilage defects, wherein the apparatus can be used with microfracture and abrasion arthroplasty.

Another object of the present invention is to provide an improved method for the repair of articular cartilage defects, wherein the method can be used with microfracture and abrasion arthroplasty.

And another object of the present invention is to provide improved apparatus for the repair of articular cartilage defects, wherein the apparatus can be used with autologous cell transplantation.

Still another object of the present invention is to provide an improved method for the repair of articular cartilage defects, wherein the method can be used with autologous cell transplantation.

These and other objects are addressed by the provision and use of the present invention which, in one form of the invention, comprises an encapsulation device adapted to encapsulate loose-bodied cells (e.g., blood and marrow cells, pluripotent stem cells, autologous cartilage cells, etc.) so as to facilitate the repair of articular cartilage defects. The encapsulation device is preferably formed out of bioabsorbable or bioremodelable materials, such that the encapsulation device will only be present at the surgical site for a limited period of time following surgery.

In another aspect of the present invention, there is provided an encapsulation device for the repair of articular cartilage defects. The device comprises a body for disposition adjacent a bone in an area of the cartilage defect, and elongated leg structure extending from the body for disposition in the bone in the area of the cartilage defect. The leg structure is provided with a length which is a plurality of magnitudes greater than a thickness of the body, and is of a generally conical configuration.

In accordance with a further feature of the invention, there is provided a system for effecting articular cartilage defect repair. The system includes an encapsulation device comprising a body for disposition adjacent a bone in an area of the cartilage defect, and elongated leg structure extending from a distal surface of the body for disposition in the bone in the area of the cartilage defect, wherein the elongated leg structure comprises one or more legs. Each leg of the leg structure is provided with a central opening therein extending from a proximal surface of the body. A pilot hole device is provided comprising a head portion, at least one elongated foot extending distally from the head portion, and a handle portion extending proximally from the head portion, the pilot hole device elongated foot being adapted to form a pilot hole in the bone to receive a leg member of the leg structure. An insertion tool is provided comprising a head portion, at least one elongated foot extending from a distal end of the head portion, each elongated foot of the insertion tool head portion being adapted to be received by the central opening of one of the encapsulation device legs. The insertion tool head portion is adapted to engage a proximal surface of the encapsulation device. The encapsulation device is adapted to be mounted on the insertion tool, and the insertion tool may be manipulated to drive the encapsulation device leg structure into at least one hole in the bone, to place the encapsulation device distal surface adjacent the bone and in the area of the cartilage defect.

In accordance with a still further feature of the invention, there is provided a tool for in-bone placement of an encapsulation device for repair of an articular cartilage defect, the device comprising a body portion and a cannulated leg extending distally from a center of a distal surface of the body portion. The tool comprises a head portion having a distal surface configured generally complementary to a proximal surface of the encapsulation device, a handle portion extending proximally from the head portion, the head portion and handle portion forming a bore extending axially of the head portion and handle portion, and an insertion spike extending through the bore and adapted to extend through the encapsulation device leg, with a pointed distal end of the spike extending distally from a distal end of the encapsulation device leg. The insertion spike is adapted to form a hole in the bone and the tool in adapted to push the encapsulation device leg into the hole and the encapsulation device body into engagement with the bone.

In accordance with a still further feature of the invention, there is provided a method for effecting a repair to an articular cartilage defect. The method includes the steps of providing an encapsulation device comprising a body for disposition adjacent a bone in an area of the cartilage defect, and an elongated leg structure extending from the body for disposition in the bone in the area of the cartilage defect, wherein the elongated leg structure comprises at least one leg, producing a hole in the bone for each leg of the encapsulation device leg structure, and driving each leg of the leg structure of the encapsulation device into a hole in the bone to bring a distal surface of the encapsulation device body into adjacency with the bone.

The above features of the invention, including various novel details of construction and combinations of parts and method steps, will now be more particularly described with reference to the accompanying drawings and pointed out in the claims. It will be understood that the particular devices and methods embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
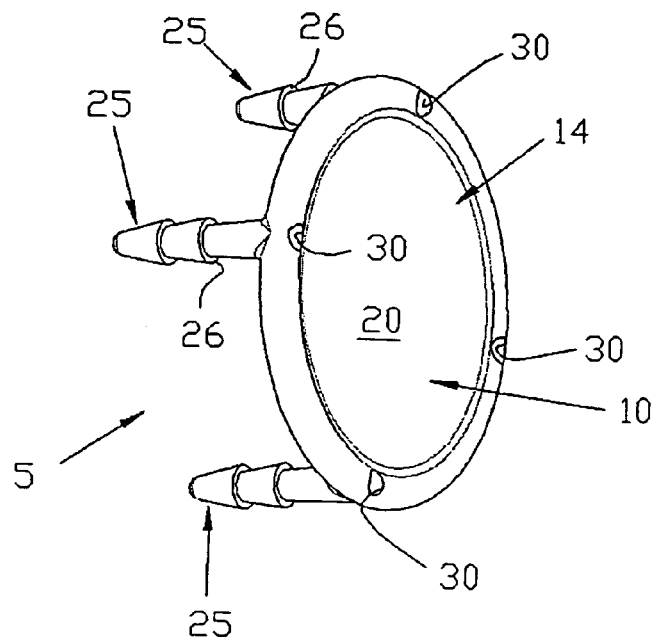
FIG. 1 is a schematic view of an encapsulation device formed in accordance with the present invention.
Figure 3:
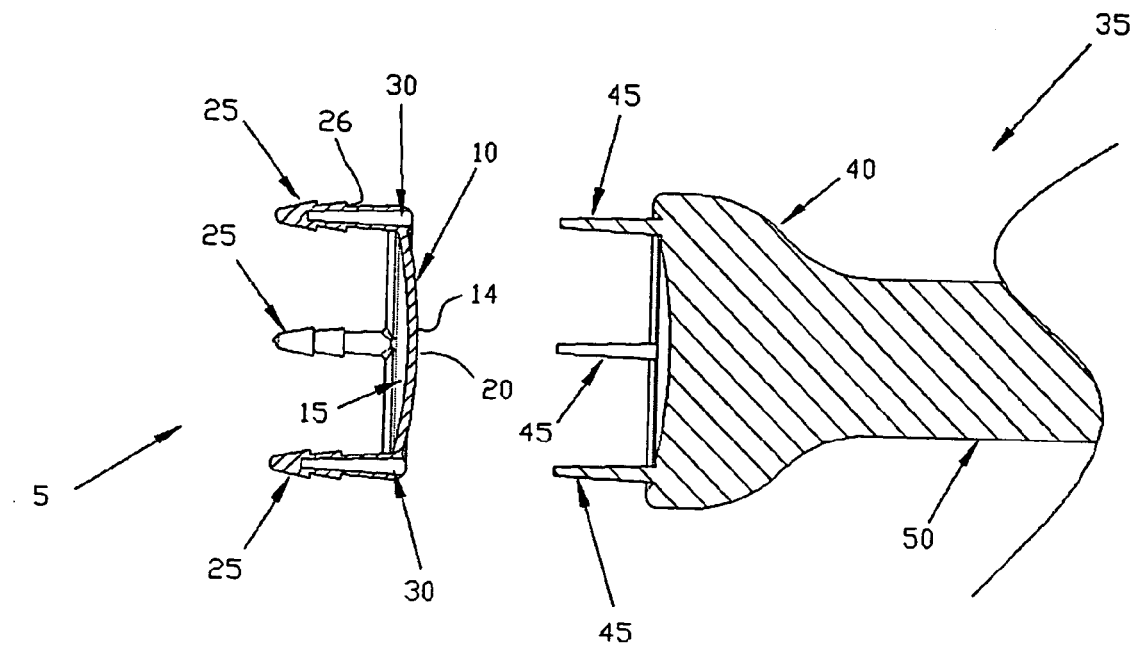
FIG. 3 is a sectional view showing the encapsulation device of FIG. 1 about to be engaged by the insertion tool of FIG. 2.

Looking first at FIG. 1, there is shown an encapsulation device 5 formed in accordance with the present invention. Encapsulation device 5 generally comprises a body 10 including a cover 14, and having a distal surface 15 (FIG. 3) and a proximal surface 20. At least one elongated leg 25 extends distally from the distal surface 15. The at least one leg 25 is of a length which is a plurality of magnitudes greater than a thickness of the body 10, to provide for secure anchoring of the body. The at least one leg 25 is preferably of a slightly conical configuration to aid in insertion of the leg into a bone, as described hereinbelow. If desired, the distal end of the at least one leg 25 may be pointed, and/or the shaft of the at least one leg 25 may be provided with locking ribs, barbs, or other protrusions, 26, so as to enhance fixation. An opening 30 is formed in the at least one leg 25 and extends through, and opens on, the body's proximal surface 20.

Encapsulation device 5 may be formed out of a single member, or it may be formed out of several members joined together during manufacture.

Encapsulation device 5 is intended to encapsulate loose-bodied cells (e.g., blood and marrow cells, pluripotent stem cells, autologous cartilage cells, etc.) so as to facilitate the repair of articular cartilage defects. To this end, encapsulation device 5 is preferably formed out of bioabsorbable or bioremodelable materials, such that the encapsulation device will only be present at the surgical site for a limited period of time following surgery (e.g., 8-12 weeks). If desired, encapsulation device 5 may be impregnated with various cell growth factors so as to assist in cell stimulation or cell regeneration.

Figure 2:
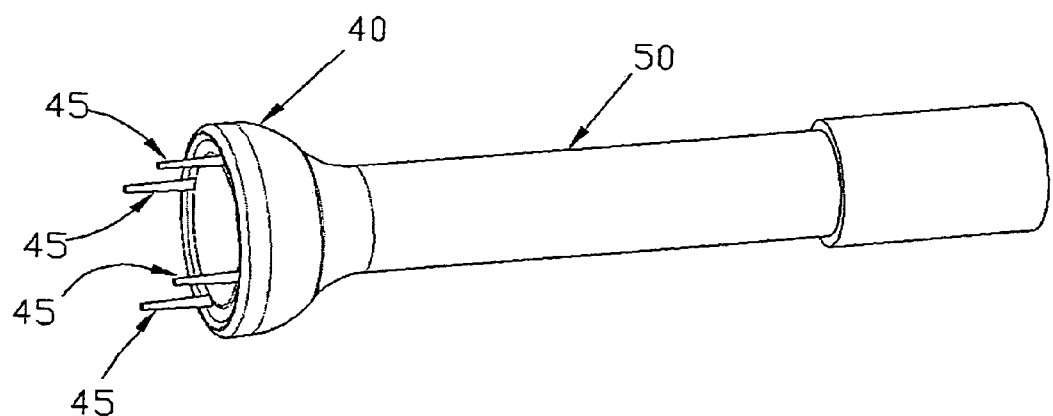
FIG. 2 is a schematic view of an insertion tool for deploying an encapsulation device of the type shown in FIG. 1.
Figure 4:
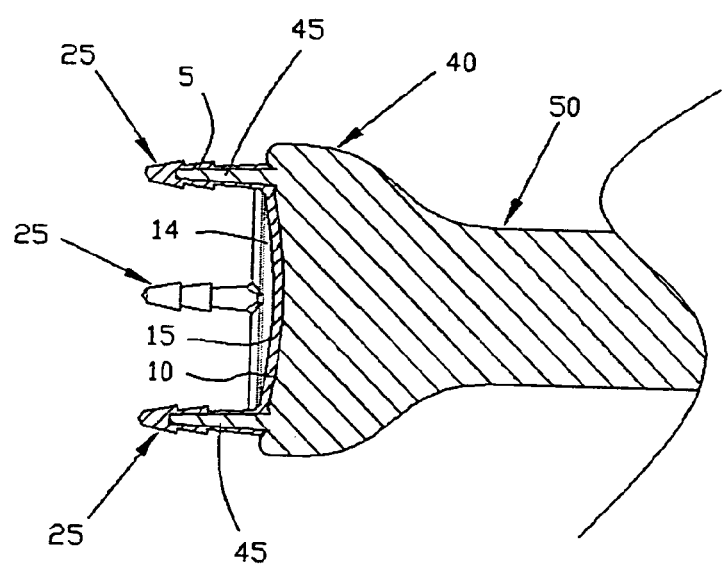
FIG. 4 is a sectional view showing the encapsulation device of FIG. 1 engaged by the insertion tool of FIG. 2.

Looking next at FIG. 2, encapsulation device 5 is intended to be deployed in the body by an insertion tool 35. Insertion tool 35 generally comprises a head 40, at least one elongated foot 45 extending distally from head 40, and a shaft 50 extending proximally from head 40. Head 40 preferably has a distal end profile generally matching the proximal end profile of the encapsulation device's body 10. The insertion tool's at least one foot 45 has a configuration which matches the encapsulation device's at least one opening 30, whereby the at least one foot 45 may be received within the at least one opening 30. To the extent that encapsulation device 5 has a plurality of legs 25 and holes 30, insertion tool 35 preferably has a plurality of feet 45, with feet 45 matching legs 25 and holes 30 in number and configuration. As a result of this construction, encapsulation device 5 may be mounted to head 40 of insertion tool 35 by passing the insertion tool's feet 45 into the encapsulation device's openings 30. See FIGS. 3 and 4. This may be done during manufacture or at the time of use. Shaft 50 permits the insertion tool to be gripped by the user and have its head 40, and hence the encapsulation device 5, directed to the surgical site.

Encapsulation device 5 may be used as follows.

Microfracture and Abrasion Arthroplasty

Figure 5:
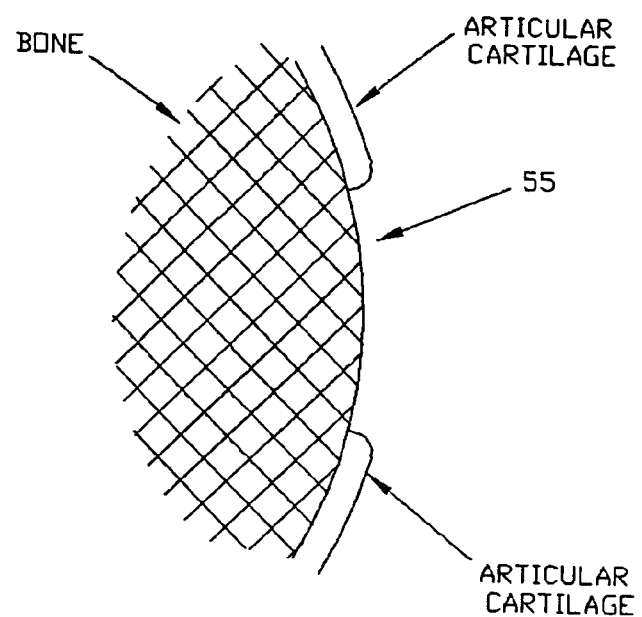
FIG. 5 is a schematic view of an articular cartilage defect.

Looking next at FIG. 5, an articular cartilage defect 55 is first prepared by microfracture or abrasion arthroplasty.

Figure 6:
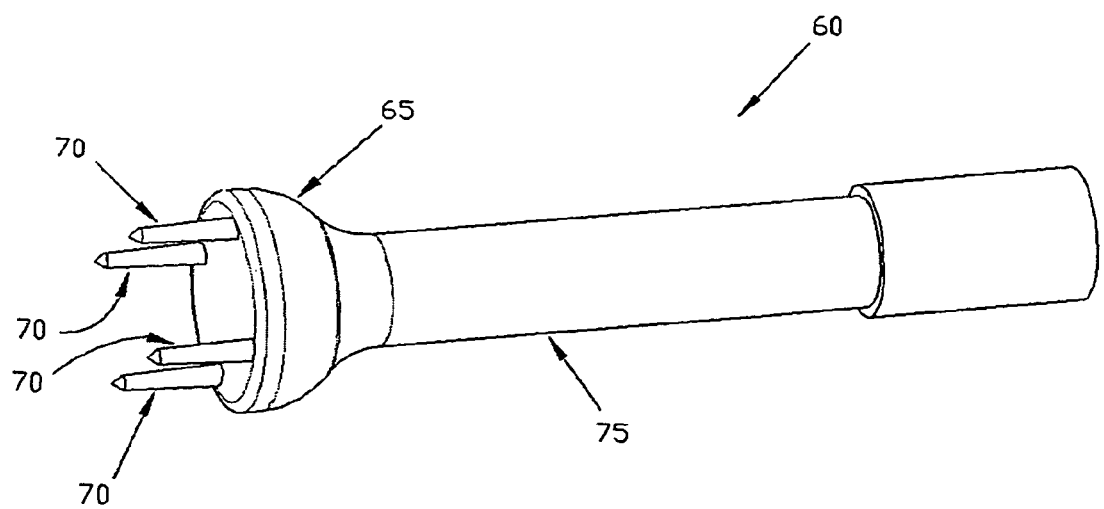
FIG. 6 is a schematic view of a pilot hole device for forming pilot holes in the articular cartilage defect shown in FIG. 5.
Figure 7:
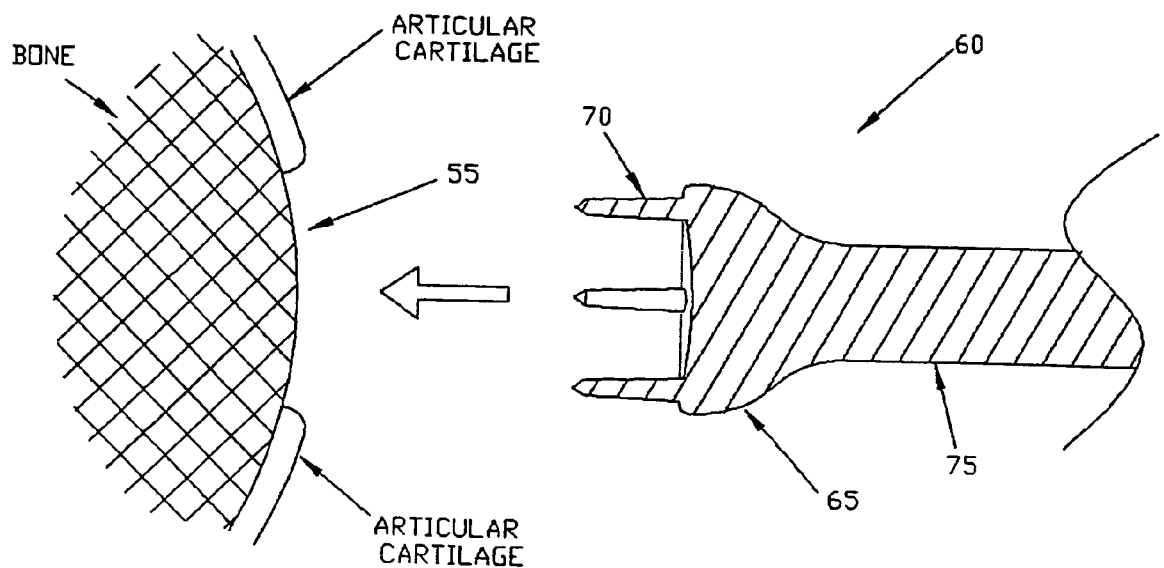
FIG. 7 is a sectional view showing the pilot hole device of FIG. 6 approaching the articular cartilage defect.
Figure 8:
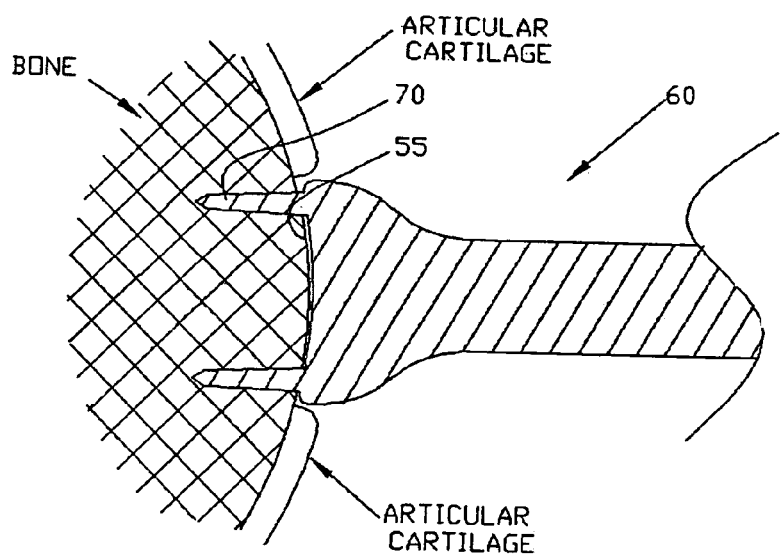
FIG. 8 is a sectional view showing the pilot hole device of FIG. 6 engaged with the articular cartilage defect.
Figure 9:
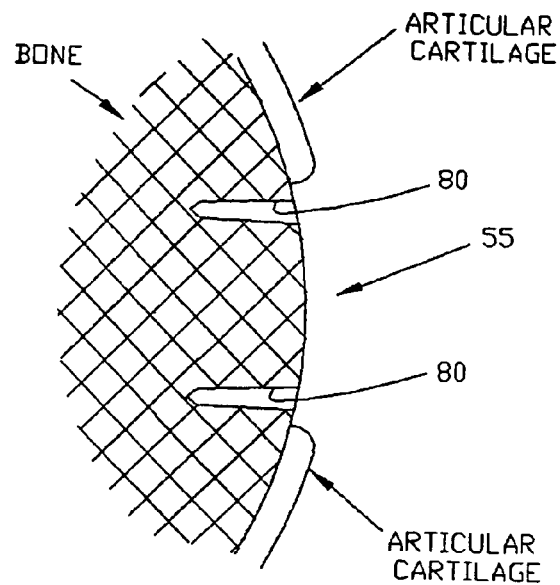
FIG. 9 is a sectional view showing the articular cartilage defect after it has had pilot holes formed therein.

Next, and looking now at FIG. 6, a pilot hole device 60, having a construction generally similar to insertion tool 35 (e.g., a head 65, at least one elongated and conically shaped foot 70 and a shaft 75) is pushed against articular cartilage defect 55 (FIGS. 7 and 8) so as to create one or more pilot holes 80 (FIG. 9). In this respect, it should be appreciated that pilot hole device 60 is constructed so as to form a pattern of pilot holes 80 which conforms to the pattern of the encapsulation device's at least one leg 25.

Figure 10:
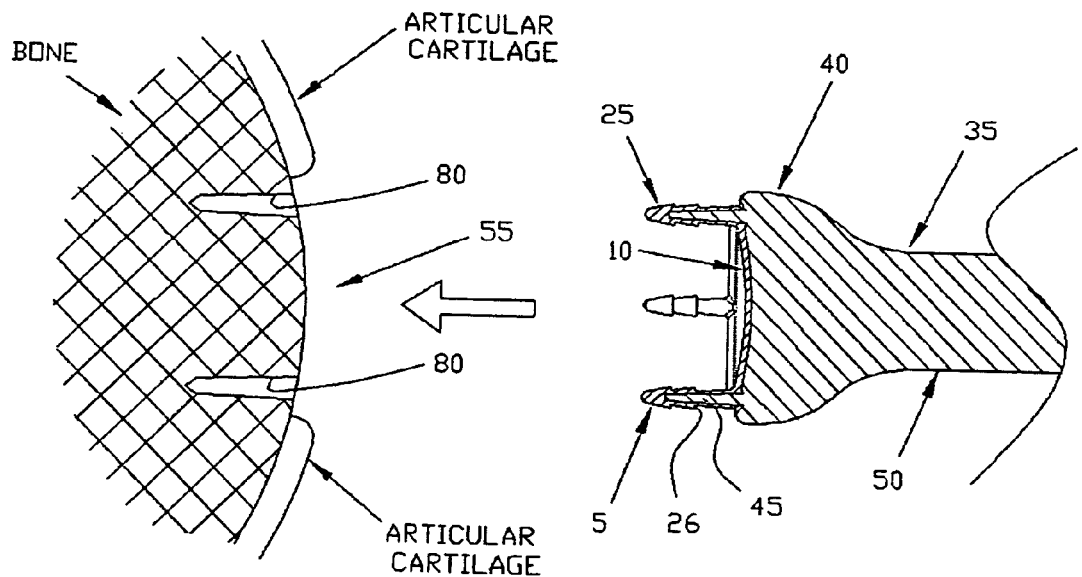
FIG. 10 is a sectional view showing the encapsulation device of FIG. 1 about to be deployed in the articular cartilage defect by the insertion tool of FIG. 2.
Figure 11:
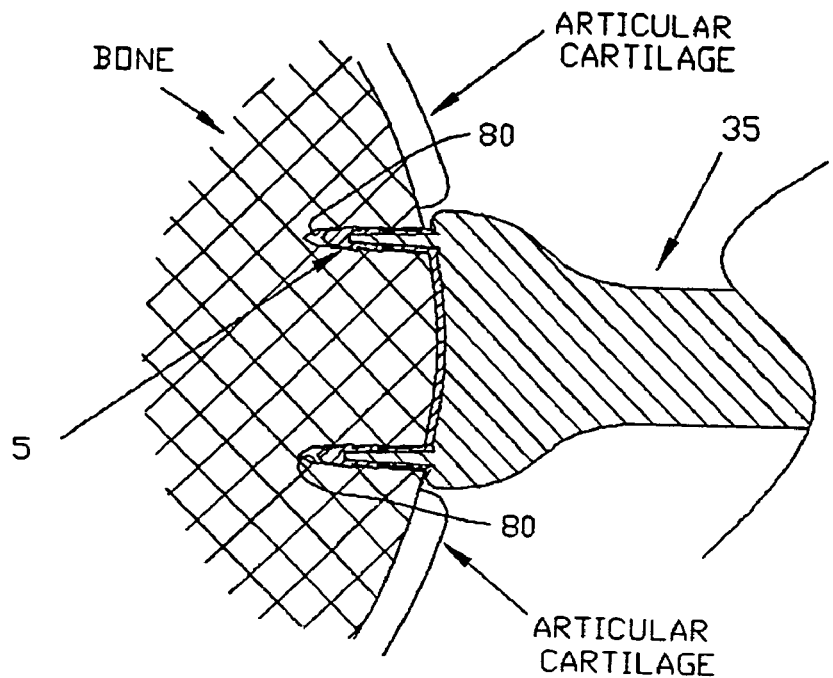
FIG. 11 is a sectional view showing the insertion tool of FIG. 2 deploying the encapsulation device of FIG. 1 in the articular cartilage defect.
Figure 12:
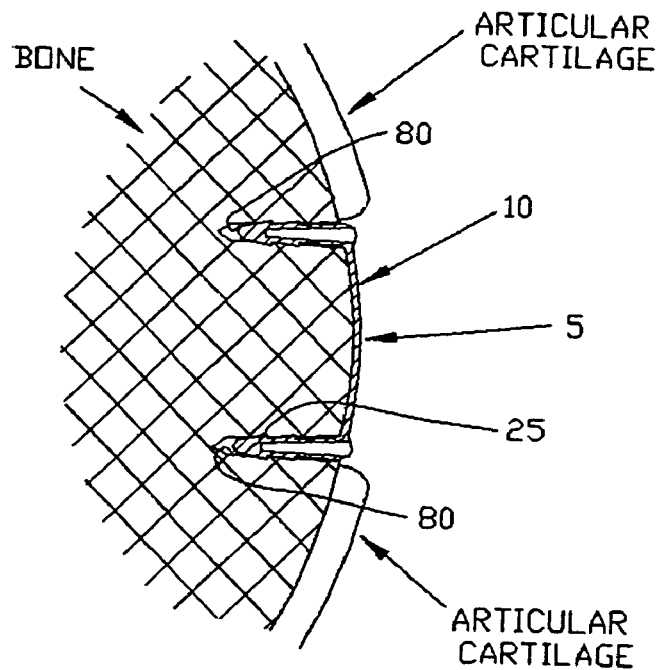
FIG. 12 is a sectional view showing the encapsulation device of FIG. 1 deployed in the articular cartilage defect, with the insertion tool of FIG. 2 having been removed from the surgical site.

Next, encapsulation device 5 is mounted to insertion tool 35 (FIG. 4), if it has not already been mounted to insertion tool 35, and then shaft 50 of insertion tool 35 is manipulated (FIGS. 10 and 11) so as to implant encapsulation device 5 directly over the treated lesion, with the encapsulation device's at least one leg 25 deployed in the at least one pilot hole 80 (FIG. 12), and with the encapsulation device's body 10 encapsulating the treated lesion, thus encouraging coagulation at the treated lesion and superior adhesion of regenerating fibrocartilage/Hyaline cartilage cells. As the cartilage cells are regenerated, encapsulation device 5 will be absorbed or remodeled, until only cartilage cells remain at the site of the original defect.

Microfracture and Abrasion Arthroplasty with Pluripotent Stem Cells

It is also possible to seed the lesion site with pluripotent stem cells prior to seating encapsulation device 5 in the lesion site, whereby the encapsulation device will encapsulate the pluripotent stem cells at the lesion site until the encapsulation device is absorbed or remodeled. In one preferred form of the invention, the pluripotent stem cells are harvested by aspirating bone marrow from various regions of the body (e.g., the femoral notch, the iliac crest, the spine, etc.) and then depositing the bone marrow on the lesion site either before, or concurrently with, deployment of encapsulation device 5. Alternatively, the harvested bone marrow may be filtered prior to seeding so as to produce a more potent slurry of pluripotent stem cells.

Autologous Cell Transplantation

It is also possible to seed the articular cartilage defect 55 with autologous articular cartilage cells prior to seating encapsulation device 5 at the defect site, whereby the encapsulation device will encapsulate the autologous articular cartilage cells at the defect site until the encapsulation device is absorbed or remodeled. In one preferred form of the invention, autologous articular cartilage cells are harvested, prepared outside the body (e.g., isolated and/or enhanced with growth factors and/or multiplied, etc.) and then deposited at the defect site, either before, or concurrently with, deployment of encapsulation device 5.

Other Alternative Embodiments

Figure 13:
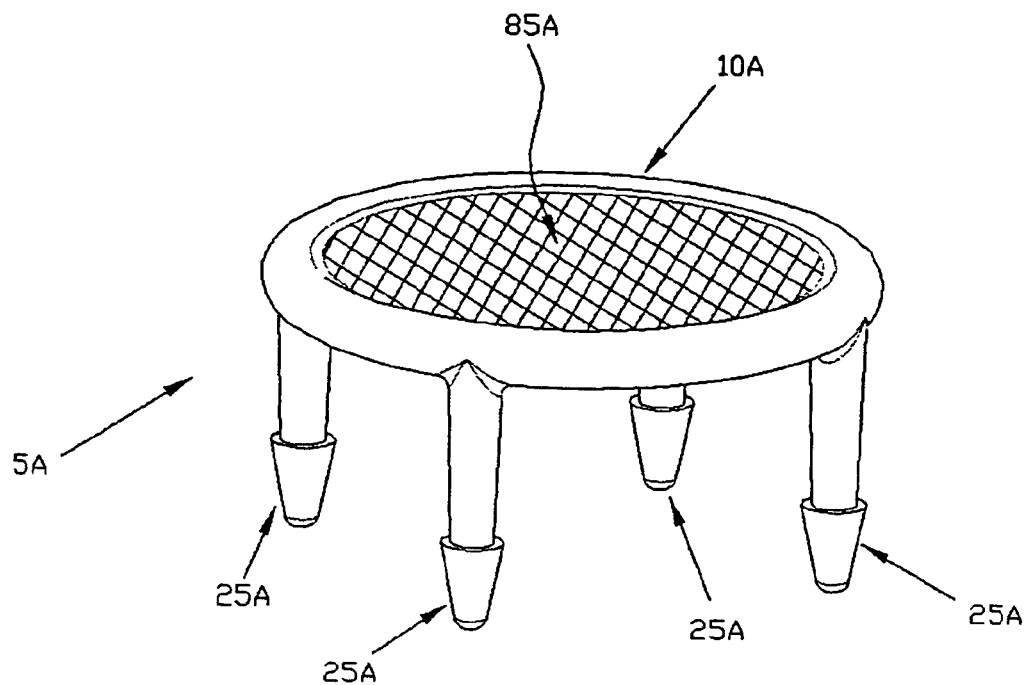
FIG. 13 is a schematic view of an alternative form of encapsulation device formed in accordance with the present invention.

Looking next at FIG. 13, there is shown an encapsulation device 5A which comprises an alternative form of the invention. Encapsulation device 5A is similar to the encapsulation device 5 described above, except that body 10A includes a matrix or mesh 85A at one or more locations within the body 10A, rather than the aforementioned cover 14. One or more legs 25A extend from the body 10A. Forming a body 10A with a matrix or mesh 85A can be advantageous over a solid body 10, e.g., in the case of microfracture and abrasion arthroplasty, it can provide a superior flow of nutrients to the site and a superior flow of waste products away from the site; or in the case of microfracture and abrasion arthroplasty with pluripotent stem cells, it can permit a slurry of such cells to be placed on the encapsulation device prior to deploying the encapsulation device at the defect site; or in the case of autologous cell transplantation, it can permit a slurry of graft articular cartilage cells to be placed on the encapsulation device prior to deploying the encapsulation device at the defect site.

Figure 14:
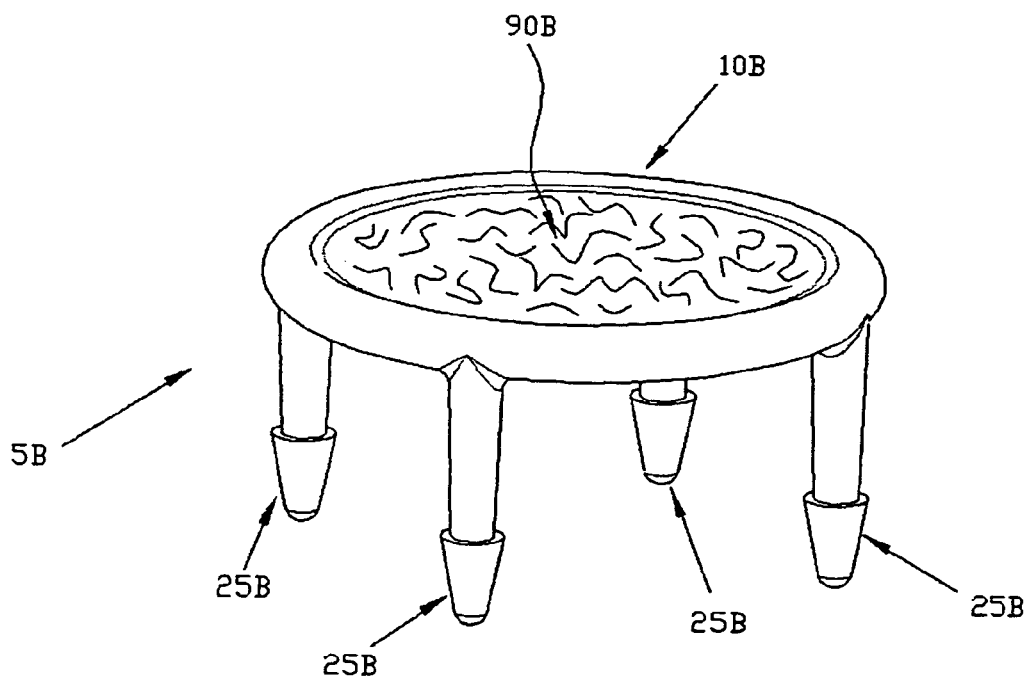
FIG. 14 is a schematic view of another alternative form of encapsulation device formed in accordance with the present invention.

Looking next at FIG. 14, there is shown an encapsulation device 5B which comprises another alternative form of the invention. Encapsulation device 5B is similar to encapsulation device 5 described above, except that body 10B thereof includes a collagen scaffold 90B for promoting the growth of replacement cartilage across the defect site.

Figure 15:
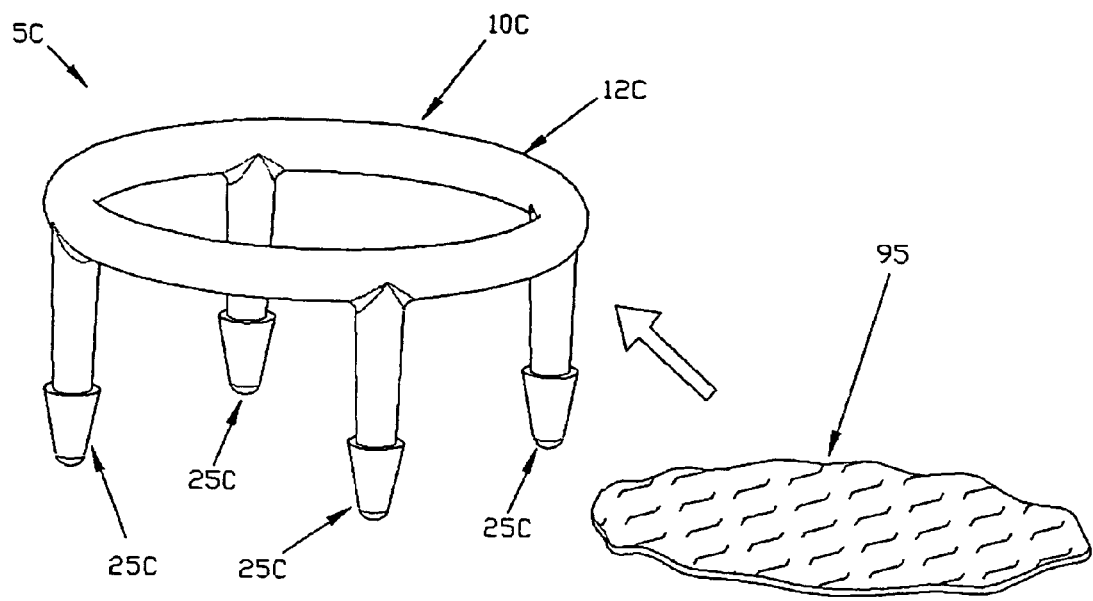
FIG. 15 is a schematic view showing still another alternative form of encapsulation device formed in accordance with the present invention, wherein the encapsulation device is adapted to have a piece of harvested periosteum secured thereto.
Figure 15A:
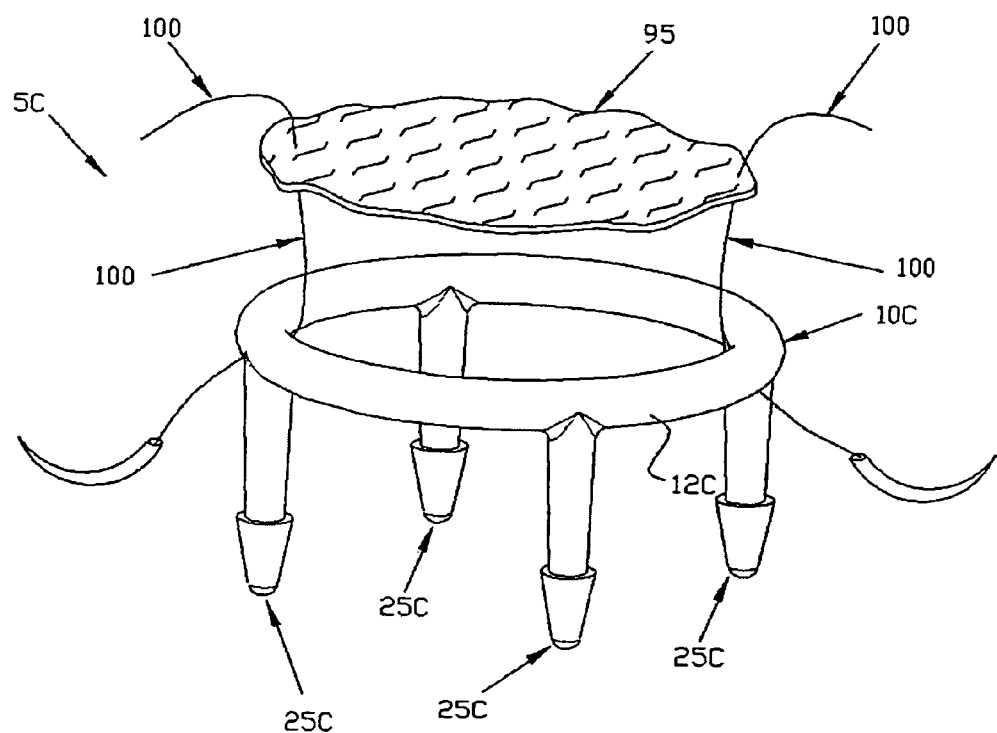
FIG. 15A is a schematic view like that of FIG. 15, except showing the piece of harvested periosteum being secured to the encapsulation device.
Figure 15B:
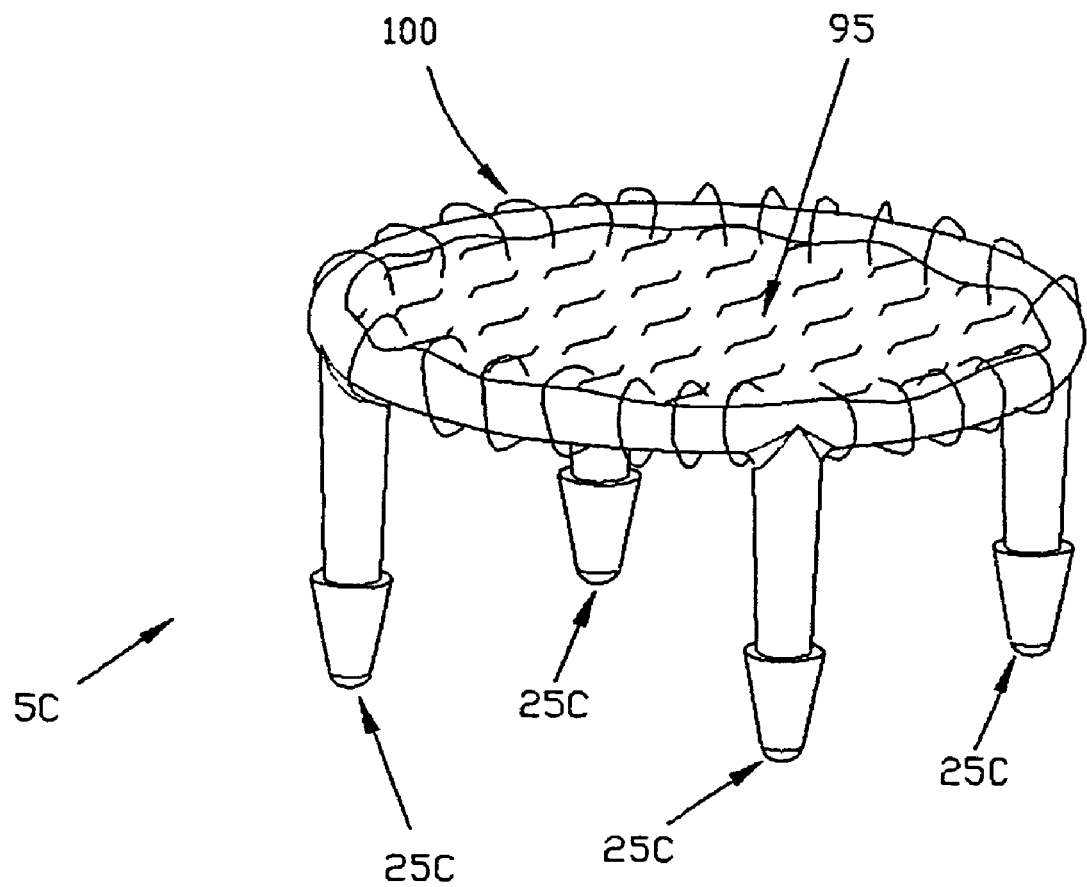
FIG. 15B is a schematic view like those of FIGS. 15 and 15A, except showing the piece of harvested periosteum secured to the encapsulation device.
Figure 16C:
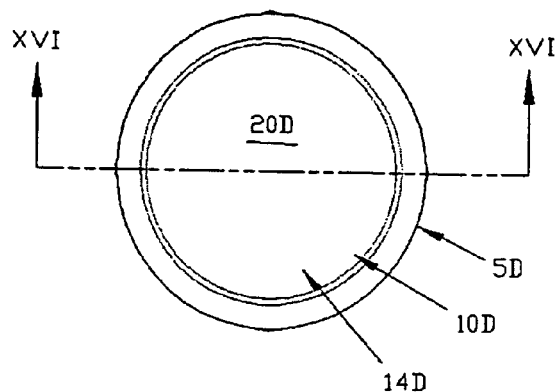
FIG. 16C is a top plan view of the device of FIGS. 16A and 16B.
Figure 16A:
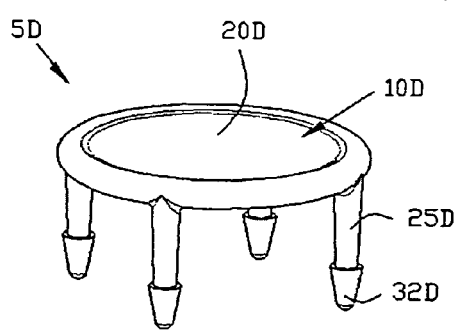
FIGS. 16A and 16B are perspective views of an alternative embodiment of the encapsulation device.
Figure 16B:
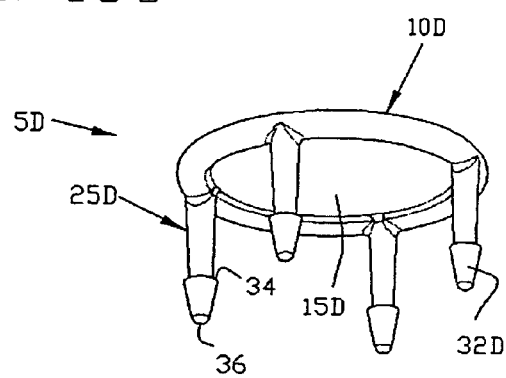
Figure 16D:
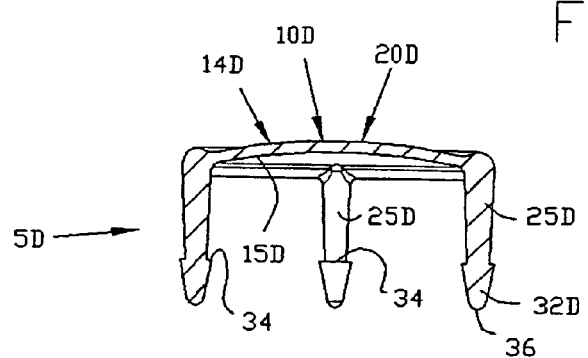
FIG. 16D is a sectional view taken along line XVI-XVI of FIG. 16C.
Figure 17C:
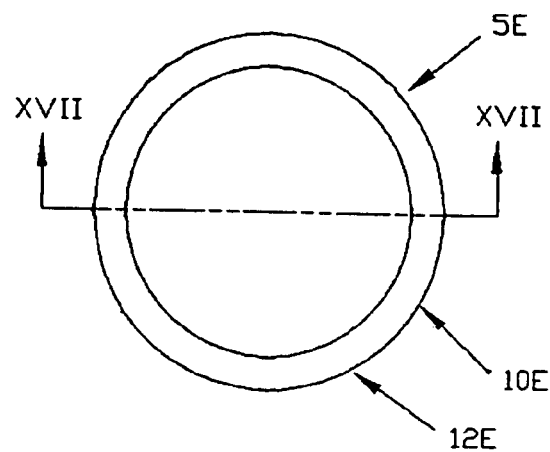
FIGS. 17A-17D are views similar to those of FIGS. 16A-16D, respectively, but illustrative of a further alternative embodiment of encapsulation device.
Figure 17A:
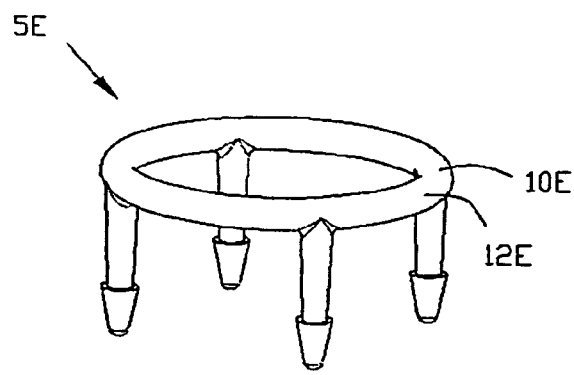
Figure 17B:
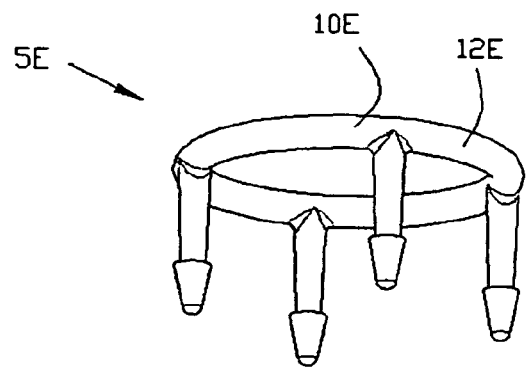
Figure 17D:
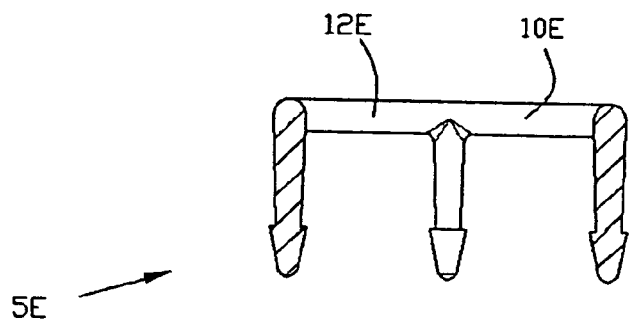
Figure 18C:
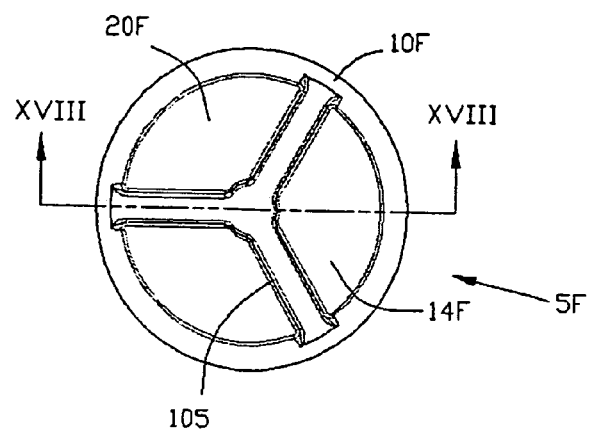
FIGS. 18A-18D are views similar to those of FIGS. 17A-17D, respectively, but illustrative of a further alternative embodiment.
Figure 18A:
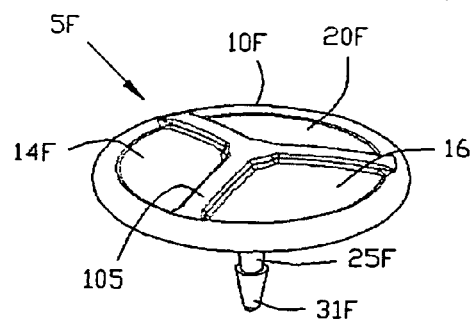
Figure 18B:
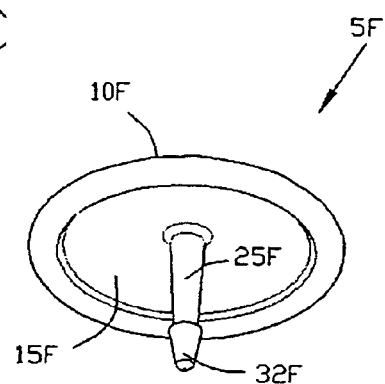
Figure 18D:
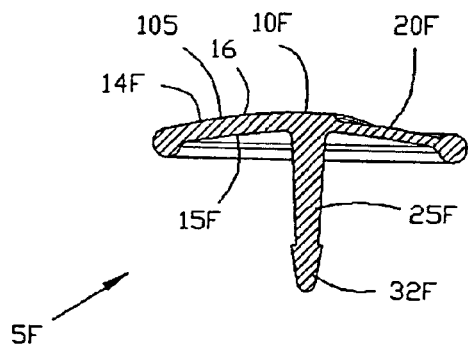
Figure 19C:
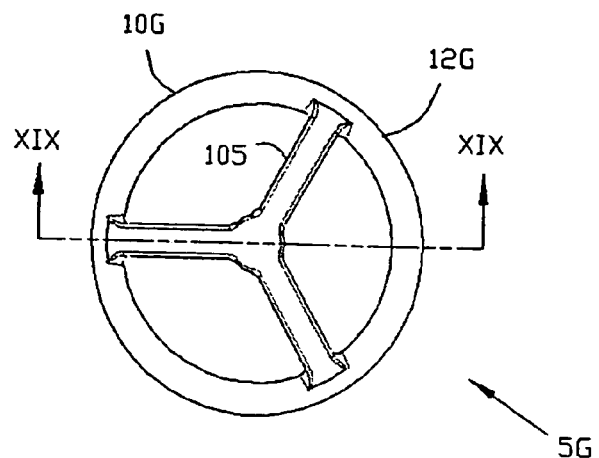
FIGS. 19A-19D are views similar to those of FIGS. 18A-18D, respectively, but illustrative of a still further alternative embodiment.
Figure 19A:
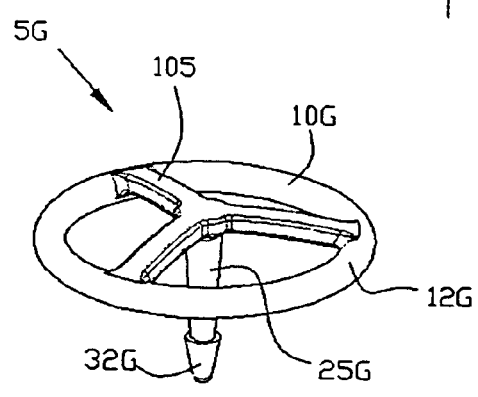
Figure 19B:
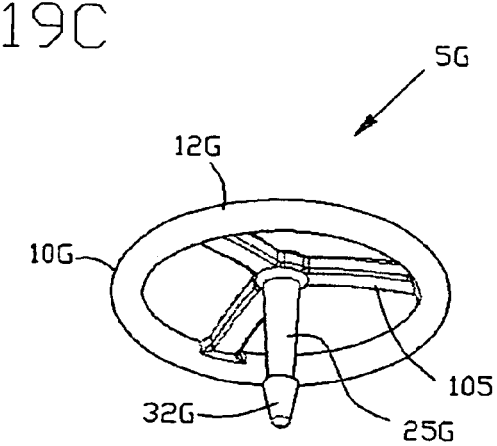
Figure 19D:
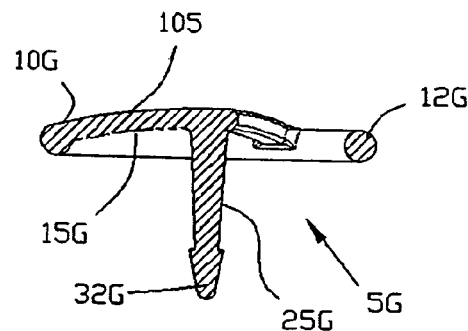
Figure 20C:
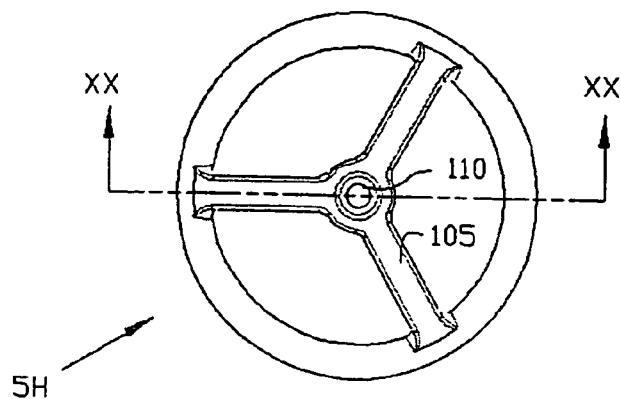
FIGS. 20A-20D are views similar to those of FIGS. 19A-19D, respectively, but illustrative of a still further alternative embodiment.
Figure 20A:
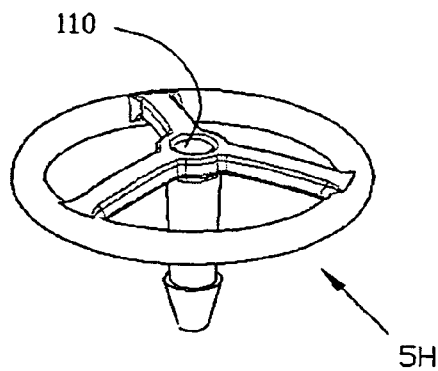
Figure 20B:
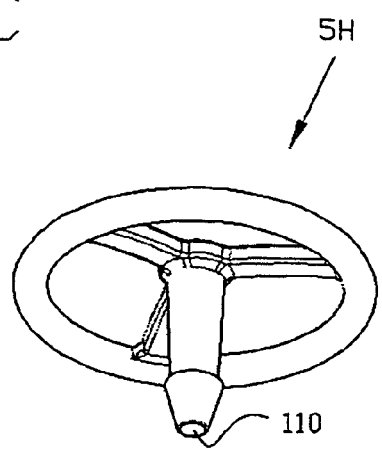
Figure 20D:
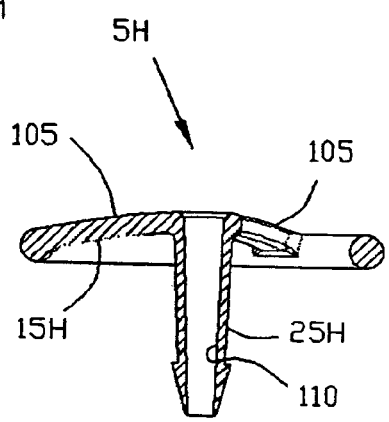
Figure 21C:
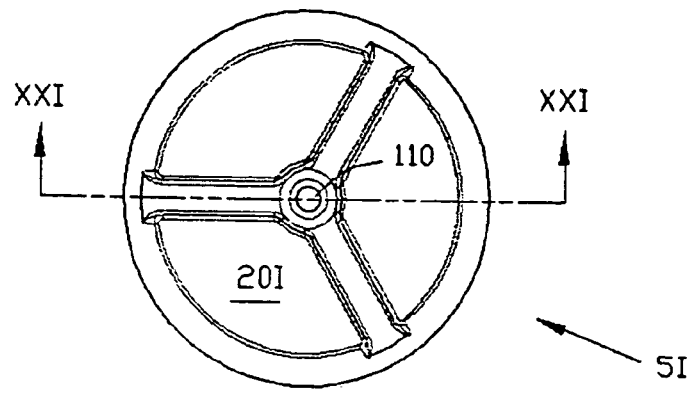
FIGS. 21A-21D are views similar to those of FIGS. 20A-20D, respectively, but illustrative of a still further alternative embodiment.
Figure 21A:
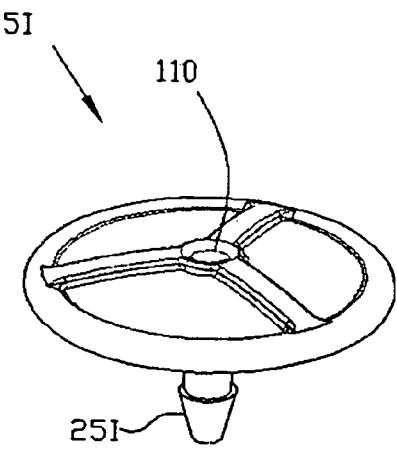
Figure 21B:
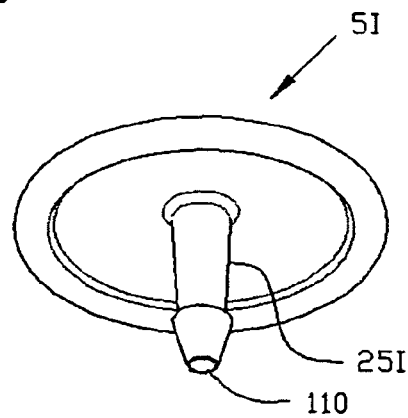
Figure 21D:
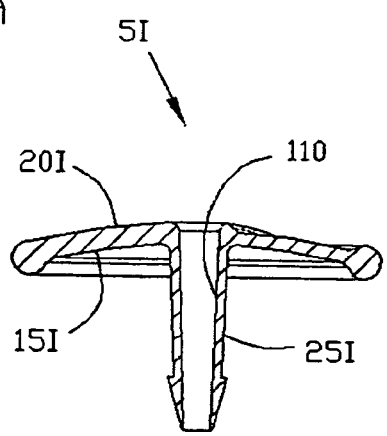

Looking next at FIG. 15, there is shown an encapsulation device 5C which comprises still another alternative form of the invention. Encapsulation device 5C is similar to the encapsulation device 5 described above, except that body 10C thereof comprises an empty frame 12C into which a mass of harvested periosteum 95 may be secured, e.g., with sutures 100 (FIGS. 15A and 15B).

Referring next to FIGS. 16A-16D, it will be seen that in an alternative embodiment of encapsulation device, 5D, body portion 10D includes a cover 14D which comprises a shell-like structure, and is provided with a distal surface 15D and a proximal surface 20D, with solid (i.e., non-cannulated) legs 25D extending distally from the distal surface 15D. The legs 25D may be provided with enlarged distal end portions 32D for increased retention properties. The enlarged end portions 32D include a proximal end 34 having a larger diameter than the adjacent portion of the leg 25D. The distal end 36 of the end portions 32D may be pointed or rounded, but are of reduced diameter. Inasmuch as legs 25D are not cannulated, encapsulation device 5D is deployed by an insertion tool (not shown) lacking the elongated feet of insertion tool 35. Such an insertion tool preferably includes means (not shown) for releasably holding the encapsulation device to the distal end of the insertion tool (e.g., a mechanical coupler, a vacuum coupler, etc.).

In FIGS. 17A-17D, there is shown another alternative embodiment of encapsulation device, 5E, generally similar to device 5D, but in which the body 10E comprises an open frame 12E, without a cover portion 14D or other similar component.

Illustrated in FIGS. 18A-18D is a further alternative embodiment of encapsulation device, 5F, in which the body 10F includes a cover portion 14F comprising a shell 16 provided with a distal surface 15F and a proximal surface 20F. A single central leg 25F extends from the distal surface 15F and is provided with an enlarged end portion 32F. The proximal surface 20F is provided with reinforcing struts 105.

Referring next to FIGS. 19A-19D, it will be seen that a further alternative embodiment features an encapsulation device 5G similar in appearance to device 5F, but in which the body 10G includes a substantially open frame 12G supporting only the reinforcing struts 105 from which depends a single central leg 25G having the enlarged distal end portion 32G.

An alternative embodiment of device, 5H, shown in FIGS. 20A-20D, is generally similar to the embodiment shown in FIGS. 19A-19D, but with a cannulated leg portion 25H depending from the struts 105. As shown in the drawings, the leg 25H may be provided with an increased diameter relative to the leg 25G to accommodate a desired central passageway 110 therethrough.

In FIGS. 21A-21D, there is shown an alternative embodiment of encapsulation device, 5I, which is similar to the device 5F shown in FIGS. 18A-18D, but in which the single depending leg 25I is provided with the axial passageway 110 therethrough.

Figure 22:
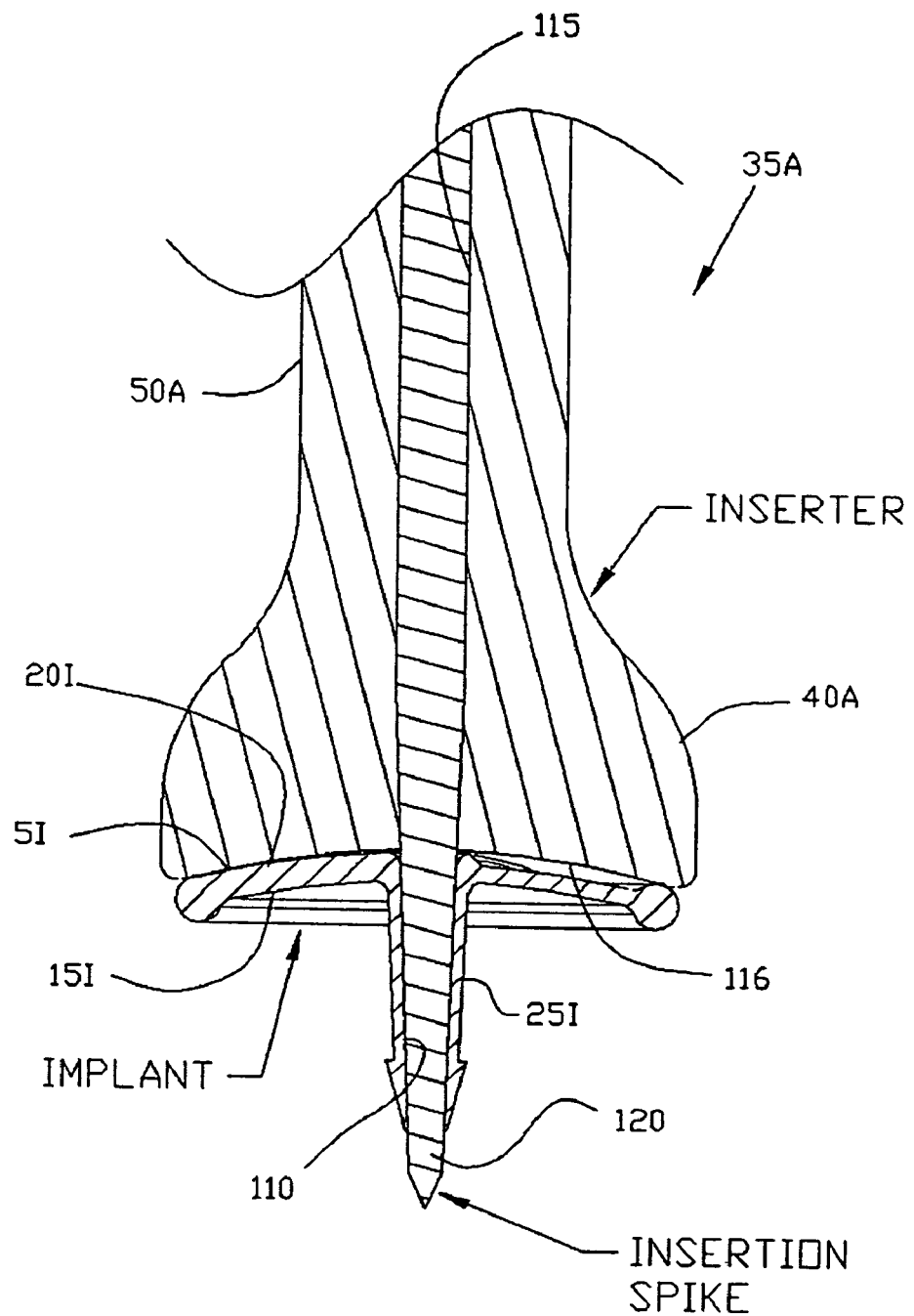
FIG. 22 is a sectional view of the encapsulation device of FIG. 21 shown in conjunction with an inserter tool.

In FIG. 22 there is shown one preferred manner in which the cannulated encapsulation devices 5H and/or 5I may be deployed, the device 5I being shown for illustrative purposes. An insertion tool 35A includes a head portion 40A and a shaft 50A. The head portion 40A is provided with a distal end surface 116 which is generally complementary in configuration to the encapsulation device proximal surface 20I. The insertion tool 35A is provided with a bore 115 in which is disposed an insertion spike 120.

Figure 22A:
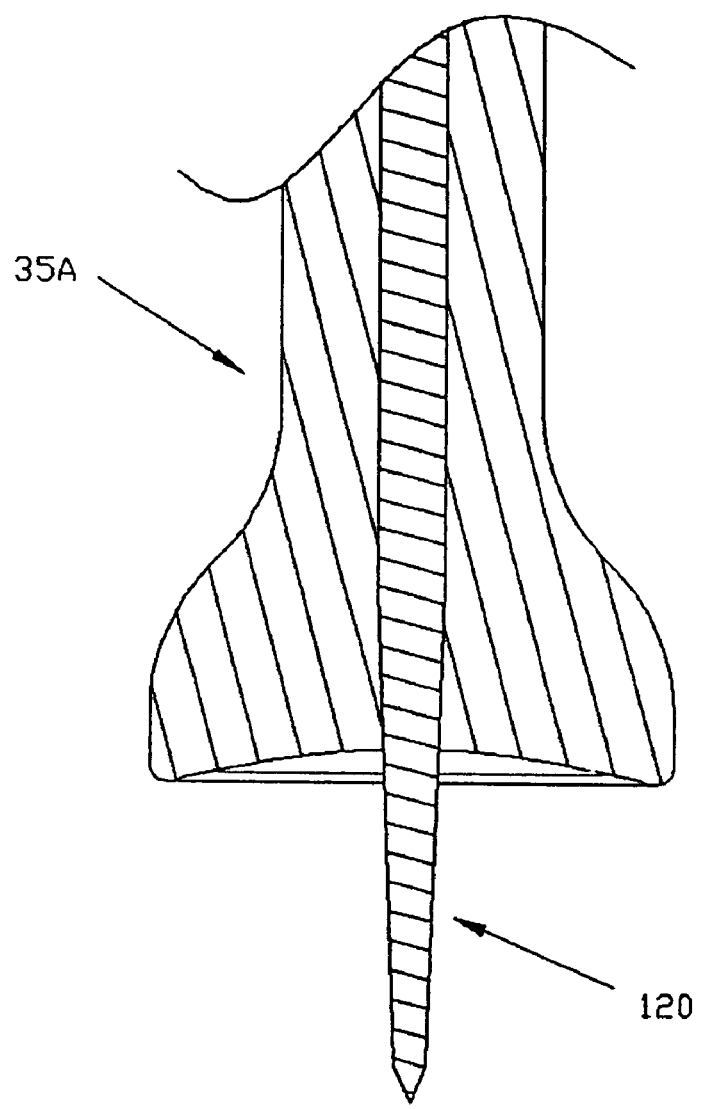
FIGS. 22A, 22B, 23 and 24 are sectional views illustrating steps in the use of the inserter tool of FIG. 22 to set the encapsulation device of FIG. 21 into bone.
Figure 22A:
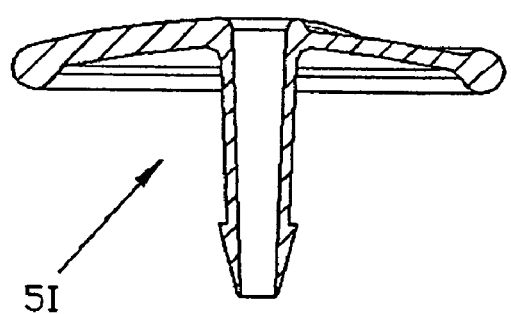
Figure 22B:
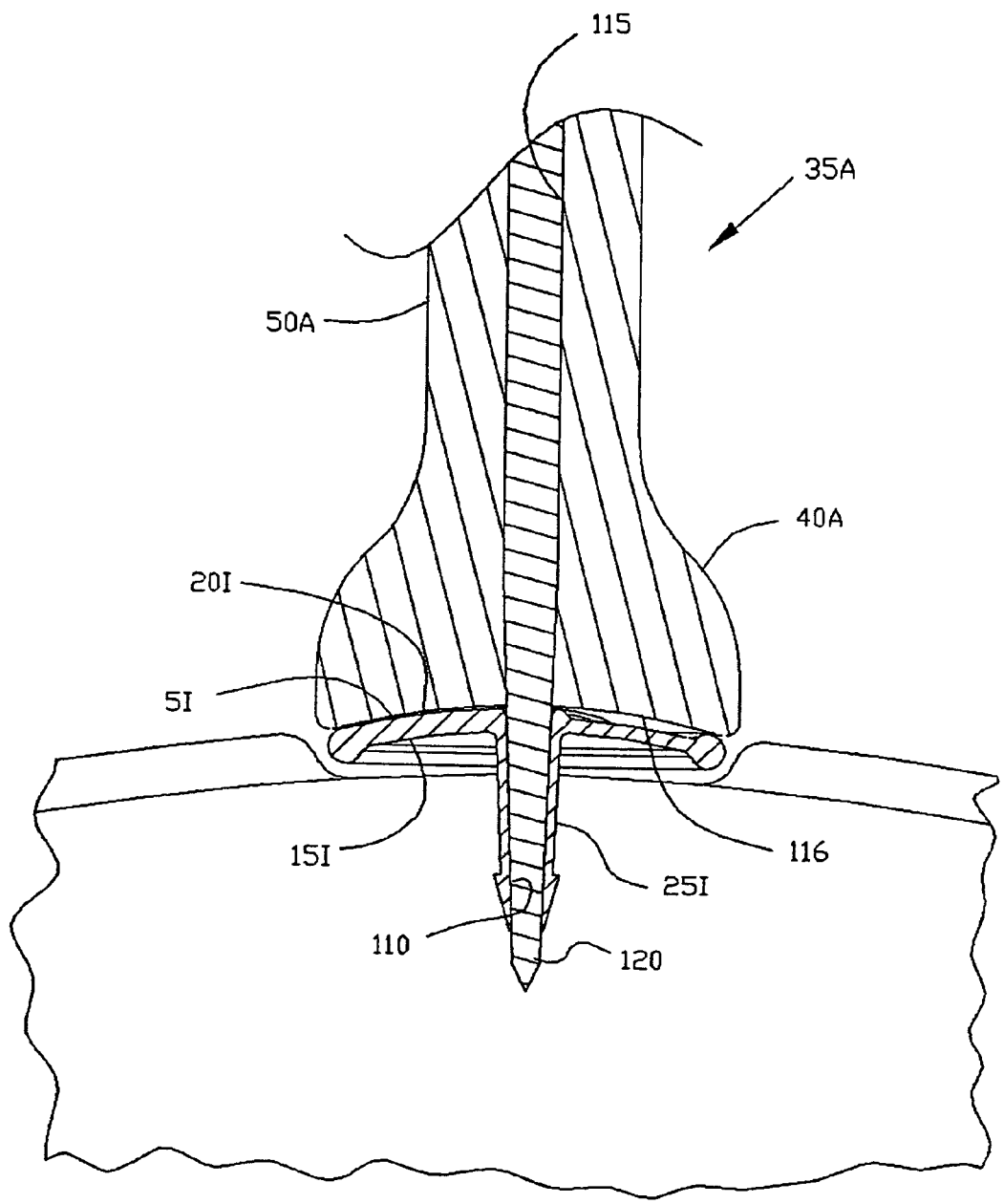
Figure 23:
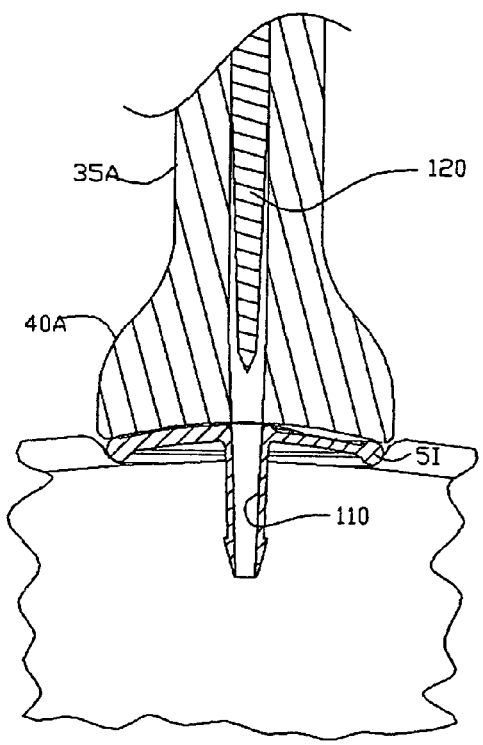
Figure 24:
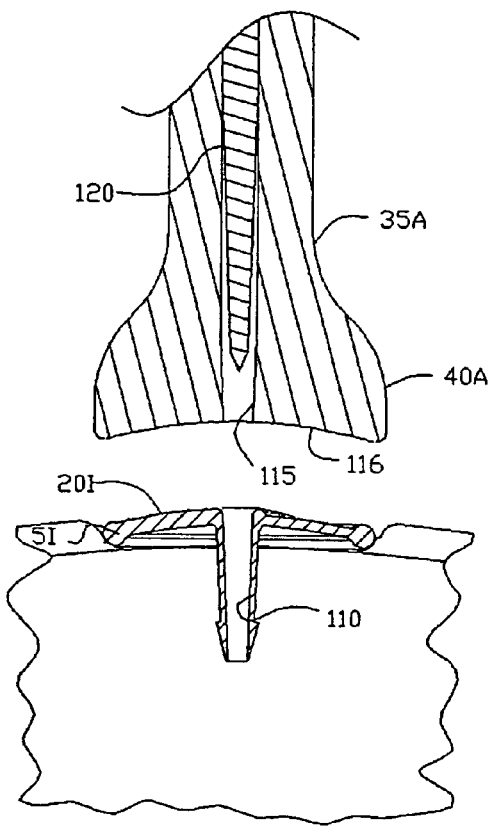

The encapsulation device axial passageway 110 receives the insertion tool insertion spike 120. The tool 35A may then be used as a combination pilot hole device and insertion tool, by punching a hole 80 and, simultaneously, introducing the device 5I into the hole. More particularly, insertion spike 120 is mounted in the insertion tool so that the distal end of the insertion spike protrudes from the distal end of the insertion tool (FIG. 22A), encapsulation device 5I is mounted to insertion tool 35A and insertion spike 120 (FIG. 22), and the assembly is advanced into the defect site (FIG. 22B). Thereafter, the insertion spike 120 is withdrawn from the device 5I (FIG. 23), and the insertion tool 35A is withdrawn from the device 5I (FIG. 24).

There is thus provided an improved apparatus and method for the repair of articular cartilage defects, which apparatus and method can be used in microfractures and abrasion arthroplasty and in autologous cell transplantation.

The encapsulation device of the present invention is ideal for full thickness defects, but it also has a role for chondromalacia, cartilage fissures, partial thickness tears, and abrasions. These lesions have a high potential for progressing into full thickness defects. The encapsulation device of the present invention, with any of the techniques described above, can be used as a temporary patch, creating a microenvironment to aid in healing and regeneration.

It will be understood that many additional changes in the details, materials, and arrangements of steps and parts, which have been herein described and illustrated in order to explain the nature of the invention, may be made by those skilled in the art within the principles and scope of the invention as expressed in the appended claims.

What is claimed is:

1. An encapsulation device for the repair of an articular cartilage defects, the device comprising:
   a body having a generally annular frame supporting therein a solid shell-like cover portion for disposition adjacent a bone in an area of the cartilage defect;
   an elongated leg structure comprising a plurality of elongated leg members fixedly connected to the body, each extending from a distal side of said body for disposition in the bone in the area of the cartilage defect, said leg members each having a length which is a plurality of magnitudes greater than a thickness of said body, and being of a generally conical configuration along substantially the length thereof;
   said annular frame comprising a peripheral frame portion, and said cover portion being integrally formed with said frame portion and disposed within said frame and of a configuration bowed proximally to always provide a bowed proximal end profile for engagement by a complementary-shaped tool head, and adapted to maintain that profile during engagement of said body with the tool head; and
   each of said leg members being provided with a central channel therein, each of the channels opening on a proximal side of said frame and extending substantially the length of each of said leg members to a point proximate a closed distal end thereof;

wherein at least one of said leg members is provided at a distal end thereof with an end portion enlarged beyond a periphery of said leg member at a proximal end of the end portion and a generally crested end portion at a distal end of the end portion.

2. The device in accordance with claim 1 wherein each of said leg member end portions comprises a circumferential protrusion thereon for gripping the bone.

3. The device in accordance with claim 1 wherein said peripheral frame portion bounds said cover portion.

4. The encapsulation device in accordance with claim 1 wherein the device is of a selected one of (i) bioabsorbable material and (ii) bioremodelable material.

5. The encapsulation device in accordance with claim 1 wherein the device is impregnated with cell growth material.

6. The encapsulation device in accordance with claim 1 wherein each of the central channels is substantially tapered along the length thereof.

7. The encapsulation device according to claim 1, wherein each of the leg members is integrally formed with the body.

8. A method for effecting a repair to an articular cartilage defect, the method comprising the steps of:
   providing an encapsulation device comprising a body for disposition adjacent a bone in an area of the cartilage defect, and an elongated leg structure comprising a plurality of elongated leg members non-rotatably extending from the body for disposition in the bone in the area of the cartilage defect, the elongated leg structure comprising legs, each leg provided with a central channel therein, the channel being open on a proximal side of the frame member and extending substantially the length of each of the leg members to a point proximate a closed distal end thereof;
   the body comprising a peripheral circular frame portion and a solid shell-like cover portion fixed within the frame portion and of a configuration bowed proximally therefrom to provide a bowed proximal surface, such that a central portion of the cover portion always extends proximally further than a peripheral portion of the cover portion;
   producing an elongated hole in the bone for each leg of the encapsulation device leg structure;
   receiving a distal end of an insertion tool within the central channels of each of the leg members; and
   non-rotatably driving each leg of the leg structure of the encapsulation device into the hole provided therefore in the bone to bring a distal surface of the bowed encapsulation device body into adjacency with the bone.

9. The method in accordance with claim 8 wherein each of the central channels is substantially tapered along the length thereof.

10. The method in accordance with claim 8 wherein each of the leg members is integrally formed with the body.

* * * * *